US009616153B2

(12) United States Patent
McKay

(10) Patent No.: US 9,616,153 B2
(45) Date of Patent: Apr. 11, 2017

(54) RIGID BONE GRAFT SUBSTITUTE

(75) Inventor: William F. McKay, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1186 days.

(21) Appl. No.: 12/104,564

(22) Filed: Apr. 17, 2008

(65) Prior Publication Data

US 2009/0265017 A1    Oct. 22, 2009

(51) Int. Cl.
*A61F 2/28* (2006.01)
*A61L 27/56* (2006.01)
*A61L 27/40* (2006.01)
*A61L 27/54* (2006.01)
*A61F 2/30* (2006.01)

(52) U.S. Cl.
CPC ............ *A61L 27/56* (2013.01); *A61F 2/2803* (2013.01); *A61L 27/40* (2013.01); *A61L 27/54* (2013.01); *A61F 2002/2817* (2013.01); *A61F 2002/30062* (2013.01); *A61F 2002/3092* (2013.01); *A61F 2002/3096* (2013.01); *A61F 2210/0004* (2013.01); *A61F 2310/00293* (2013.01); *A61F 2310/00365* (2013.01); *A61L 2300/414* (2013.01); *A61L 2430/02* (2013.01)

(58) Field of Classification Search
CPC ...... A61F 2002/2803; A61F 2002/2835; A61F 2/2846; A61F 2/2803
USPC ......... 623/16.11, 17.11, 17.16, 17.17–17.19, 623/23.51, 23.56, 23.61, 23.63
See application file for complete search history.

(56) References Cited

U.S. PATENT DOCUMENTS

| | | |
|---|---|---|
| 3,944,655 A | 3/1976 | Levin et al. |
| 4,394,370 A | 7/1983 | Jefferies |
| 4,472,840 A | 9/1984 | Jefferies |
| 4,563,489 A | 1/1986 | Urist |
| 4,623,553 A | 11/1986 | Ries et al. |
| 4,698,326 A | 10/1987 | Sauk et al. |
| 4,755,593 A | 7/1988 | Lauren |

(Continued)

FOREIGN PATENT DOCUMENTS

| | | |
|---|---|---|
| EP | 1025871 A1 | 8/2000 |
| WO | WO9103491 A1 | 3/1991 |

(Continued)

OTHER PUBLICATIONS

Haid, Jr., et al., Posterior Lumbar Interbody Fusion Using Recombinant Human Bone Morphogenetic Protein Type With Cylindrical Interbody Cages; The Spinal Journal, vol. 4, No. 5, pp. 527-538 (2004).

(Continued)

*Primary Examiner* — Christian Sevilla
*Assistant Examiner* — Megan Wolf

(57) ABSTRACT

A bone graft substitute includes a porous matrix at least partially covered by a reinforcing outer layer. The porous matrix may be a collagen-ceramic composite, and the reinforcing outer layer may be formed from highly cross-linked collagen. The implant may also include one or more reinforcement ribs, which may be made from calcium phosphate or dense collagen. In addition, the bone graft substitute preferably includes an effective amount of a bioactive agent, such as BMP-2, rhBMP-2, or functional fragments thereof. The bioactive agent is preferably disposed within the porous matrix.

12 Claims, 13 Drawing Sheets

(56) References Cited

U.S. PATENT DOCUMENTS

| | | | |
|---|---|---|---|
| 4,780,450 A | 10/1988 | Sauk et al. | |
| 4,795,467 A * | 1/1989 | Piez | A61L 27/46 424/423 |
| 4,863,472 A * | 9/1989 | Tormala et al. | 623/23.58 |
| 4,865,602 A | 9/1989 | Smestad et al. | |
| 4,963,145 A | 10/1990 | Takagi et al. | |
| 5,043,426 A | 8/1991 | Goldstein | |
| 5,231,169 A | 7/1993 | Constantz et al. | |
| 5,238,491 A | 8/1993 | Sugihara et al. | |
| 5,246,457 A | 9/1993 | Piez et al. | |
| 5,320,844 A | 6/1994 | Liu | |
| 5,385,887 A * | 1/1995 | Yim et al. | 514/8.8 |
| 5,425,770 A | 6/1995 | Piez et al. | |
| 5,455,231 A | 10/1995 | Constantz et al. | |
| 5,508,267 A | 4/1996 | Czernuszka et al. | |
| 5,531,791 A | 7/1996 | Wolfinbarger, Jr. | |
| 5,532,217 A | 7/1996 | Silver et al. | |
| 5,597,578 A | 1/1997 | Brown et al. | |
| 5,674,292 A | 10/1997 | Tucker et al. | |
| 5,707,962 A | 1/1998 | Chen et al. | |
| 5,739,286 A | 4/1998 | Silver et al. | |
| 5,776,193 A | 7/1998 | Kwan et al. | |
| 5,916,870 A | 6/1999 | Lee et al. | |
| 6,013,856 A | 1/2000 | Tucker et al. | |
| 6,028,242 A | 2/2000 | Tucker et al. | |
| 6,180,606 B1 | 1/2001 | Chen et al. | |
| 6,187,047 B1 | 2/2001 | Kwan et al. | |
| 6,300,315 B1 | 10/2001 | Liu | |
| 6,311,690 B1 | 11/2001 | Jefferies | |
| 6,379,962 B1 | 4/2002 | Holy et al. | |
| 6,409,764 B1 * | 6/2002 | White et al. | 623/16.11 |
| 6,417,166 B2 | 7/2002 | Liu | |
| 6,461,630 B1 | 10/2002 | Tucker et al. | |
| 6,485,751 B1 | 11/2002 | Wang | |
| 6,504,079 B2 | 1/2003 | Tucker et al. | |
| 6,764,517 B2 | 7/2004 | Yamamoto et al. | |
| 6,902,584 B2 | 6/2005 | Kwan et al. | |
| 6,969,523 B1 | 11/2005 | Mattern et al. | |
| 2001/0014830 A1 | 8/2001 | Kwan et al. | |
| 2002/0055143 A1 | 5/2002 | Bell et al. | |
| 2002/0106411 A1 | 8/2002 | Wironen et al. | |
| 2002/0183855 A1 | 12/2002 | Yamamoto et al. | |
| 2003/0031698 A1 | 2/2003 | Roeder et al. | |
| 2003/0036797 A1 * | 2/2003 | Malaviya et al. | 623/14.12 |
| 2004/0033249 A1 | 2/2004 | Sewing et al. | |
| 2004/0109937 A1 | 6/2004 | Jennissen et al. | |
| 2004/0220680 A1 | 11/2004 | Yamamoto et al. | |
| 2005/0020506 A1 | 1/2005 | Drapeau et al. | |
| 2005/0064007 A1 | 3/2005 | Steinemann et al. | |
| 2005/0217538 A1 | 10/2005 | Reinstorf et al. | |
| 2005/0249773 A1 * | 11/2005 | Maspero et al. | 424/423 |
| 2006/0029591 A1 | 2/2006 | Vukicevic et al. | |
| 2006/0039947 A1 | 2/2006 | Schmidmaier et al. | |
| 2006/0292350 A1 * | 12/2006 | Kawamura et al. | 428/189 |
| 2007/0129807 A1 * | 6/2007 | Lynch et al. | 623/17.17 |
| 2008/0147065 A1 | 6/2008 | McKay et al. | |
| 2008/0154372 A1 | 6/2008 | Peckham | |

FOREIGN PATENT DOCUMENTS

| | | |
|---|---|---|
| WO | WO0124842 A2 | 4/2001 |
| WO | WO0170288 A2 | 9/2001 |
| WO | WO0178685 A1 | 10/2001 |
| WO | WO03066083 A1 | 8/2003 |

OTHER PUBLICATIONS

Lind, et al., Effect of Osteogenic Protein 1/Collagen Composite Combined With Impacted Allograft Around Hydroxyapatite-Coated Titanium Alloy Implants is Moderate; J. Biomed Mater Res., 1:89-98 (Apr. 2001).

* cited by examiner

RIGID BONE GRAFT SUBSTITUTE

FIELD OF THE INVENTION

The present invention relates generally to bone graft substitutes. More particularly, the present invention discloses a bone graft substitute having a matrix that permits rapid bone in-growth that is covered with a rigid outer jacket to help maintain the shape of the substitute.

BACKGROUND OF THE INVENTION

The use of carrier matrices to promote the formation of bone at a site in a patient is well known, and related products are currently available on the market, such as Mastergraft® Putty and Mastergraft® Matrix, both by Medtronic Sofamor Danek (Memphis, Tenn.). These matrices are typically in the form of a relatively large, soft collagen sponge or dry cake that is wetted and then packed into the bone defect.

A significant problem associated with bone regeneration when using such matrices is the lack of a suitable scaffolding material that can retain its shape and stay within the bone defect during the healing process but which is also compatible with the body. Accordingly, there is a need for improved bone graft substitutes for the repair of bone defects that are capable of retaining their shapes as new bone is generated of sufficient volume within the bone defect.

SUMMARY OF THE INVENTION

It is therefore an object to provide an implant, and a method of manufacturing related thereto, that is able to retain its shape as new bone is generated of sufficient volume in a bone defect, and specifically within the implant itself.

Various embodiments disclose a bone graft substitute that includes a porous matrix and a reinforcing outer layer that covers at least a portion of the porous matrix. In preferred embodiments the porous matrix is a collagen-ceramic composite, in which the ceramic comprises calcium phosphate, and the reinforcing outer layer is a separate material formed from highly cross-linked collagen. In another embodiment the reinforcing outer layer may also contain calcium phosphate particles in the collagen to provide additional stiffness. In certain specific embodiments the reinforcing outer layer comprises at least one opening that exposes the porous matrix.

Certain embodiments further include at least one reinforcement rib. The reinforcement rib may be at least partially surrounded by the porous matrix and the reinforcing outer layer. In some embodiments the reinforcement rib comprises a hole or hollow region. In specific preferred embodiments the reinforcement rib is formed from calcium phosphate or dense collagen. The reinforcement rib may also be integrally formed with the reinforcing outer layer, so that the reinforcement rib and outer layer are formed from the same material, and optionally at the same time.

In various embodiments, the bone graft substitute further includes an effective amount of a bioactive agent. In specific embodiments, the bioactive agent is selected from one or more of BMP-2, rhBMP-2, BMP-4, rhBMP-4, BMP-6, rhBMP-6, BMP-7, rhBMP-7, GDF-5, rhGDF-5, functional fragments thereof, and combinations thereof. The bioactive agent is preferably disposed within the porous matrix.

In another aspect, an embodiment method for forming an implant comprises obtaining a biocompatible outer layer, contacting a slurry comprising collagen and a ceramic material with the outer layer, and then freeze-drying the combination of the outer layer contacted with the slurry. In various embodiment methods, contacting the slurry with the outer layer comprises disposing the slurry into a mold holding the outer layer. In other embodiments, contacting the slurry with the outer layer comprises disposing the slurry into a hollow region formed by the outer layer. In other embodiments, the method further includes contacting a biocompatible reinforcement rib with the outer layer.

DETAILED DESCRIPTION OF THE INVENTION

An improved bone graft substitute, an embodiment of which includes a matrix surrounded by a dense outer layer is disclosed. In particular, one embodiment provides a bone graft substitute that includes a collagen-ceramic composite matrix covered by a reinforcing outer layer.

To aid in an understanding of the various disclosed embodiments, the following non-limiting definitions are provided.

The term "patient" refers to a biological system to which a treatment can be administered. A biological system can include, for example, an individual cell, a set of cells (e.g., a cell culture), an organ, or tissue. Additionally, the term "patient" can refer to animals, including, without limitation, humans.

The term "treating" or "treatment" of an injury or disease refers to executing a protocol, which may include administering one or more drugs, implants or the like to a patient in an effort to repair an injury or alleviate signs or symptoms of a disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

Figure 1:
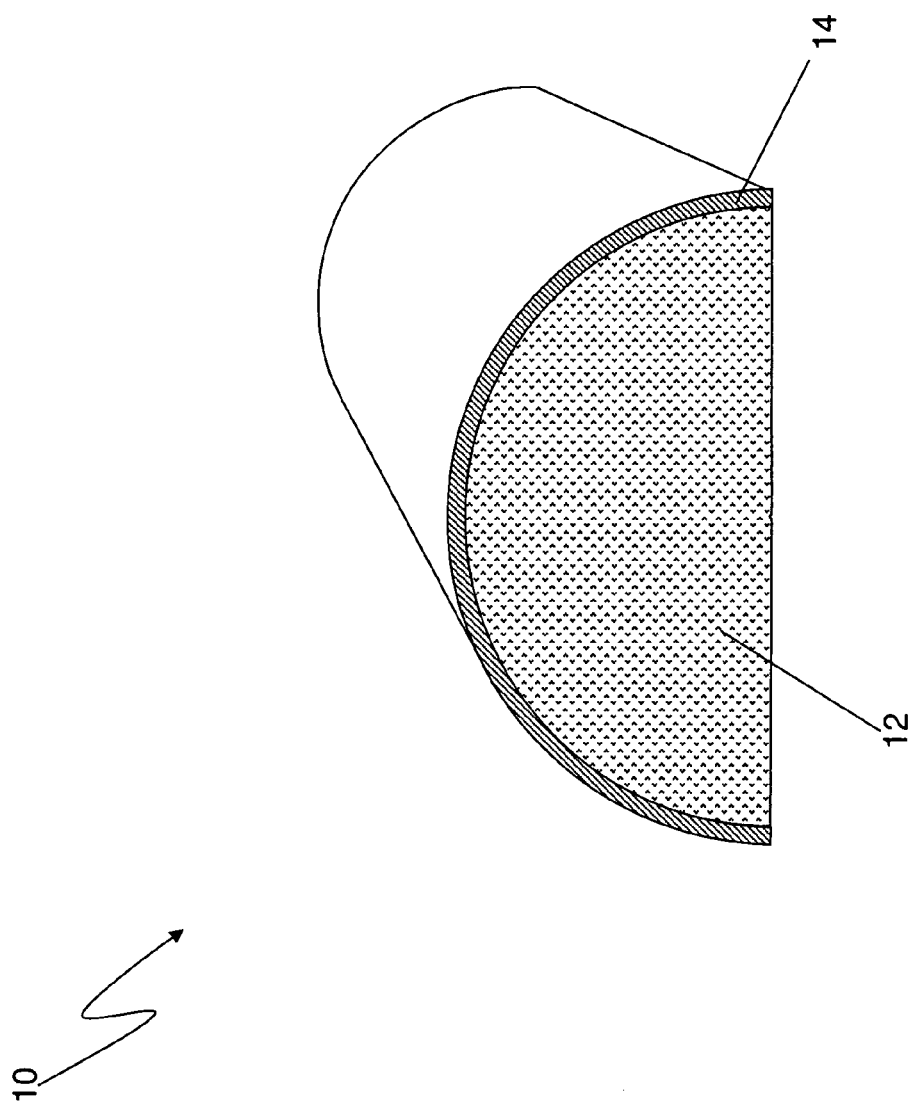
FIG. 1 is perspective view of a first embodiment bone graft substitute.

Please refer to FIG. 1, which is a perspective view of an embodiment bone graft substitute 10. The substitute 10 is designed to be implanted into a bone defect within a patient to treat the bone defect and includes a porous matrix 12 that is at least partially covered by a reinforcing layer 14. The porosity of the matrix 12 permits rapid bone in-growth into its structure. In specific embodiments, the matrix 12 may have macropores that are 25 to 1000 microns in size, and may also have micropores that are 0.1 to 5 microns in size. The pores are preferably interconnected. The reinforcing layer 14 provides mechanical rigidity, reinforcement or preferably both to help the substitute 10 retain its shape over time as new bone forms within the matrix 12. In particular, the reinforcing outer layer 14 resists soft tissue compression. In certain embodiments, the layer 14 resists deformation under pressures of 1 psi or less. In preferred embodiments, the layer 14 resists deformation under pressures of up to 20 psi. Both the matrix 12 and the layer 14 are made from biocompatible materials, and in preferred embodiments from biodegradable materials.

The layer 14 may be provided a shape that is conformal to a target region into which the substitute 10 is to be implanted. However, prior to implantation, the substitute 10 may be additionally shaped, as by carving or cutting away regions to provide a snug fit. Additionally, once the internal porous matrix 12 is hydrated it will be deformable along its width because it is inherently less rigid in that direction, and hence may be snugly wedged into position.

In certain preferred embodiments the layer 14 is made from highly cross-linked collagen that biodegrades over an extended period of time within the patient. Such cross-linking may slow resorption of the layer 14 by up to about 6 to 8 weeks. In specific embodiments, the shrinkage temperature of the highly cross-linked collagen 14, as measured, for example, by differential scanning calorimetry, exceeds 50° C. By way of example, the layer 14 may be made separately first by first mechanically forming and cross-linking a collagen solution. The collagen solution may be, for example, a mixture of collagen, water and optional excipients. Mechanically forming the collagen solution, which may be a thick or viscous fluid, may involve any suitable steps, such as by pouring the solution into flat sheet trays to form a flat sheet, and then subsequently shaping this sheet into a desired shape and then cross-linking the sheet so that it retains the desired shape. For example, a flat sheet of collagen could be formed and then subsequently laid on top of convex curved mold, or within any suitably shaped mold, to attain the desired final shape. Once shaped, the shaped collagen sheet may then be cross-linked to retain the desired shape. By way of another example, the collagen sheet could be extruded through, or flattened by, rollers, which would expel water from the collagen solution. The resultant sheet could then be formed and cross-linked to obtain and keep the desired shape. Cross-linking of the mechanically formed solutions may be performed, for example, chemically or thermally. In some embodiments, cross-linking of the layer 14 is performed by heavily chemically cross-linking the mechanically formed solutions with formaldehyde vapor and then de-gassing the end-product to remove any residual chemical or with EDC. Thermal cross-linking of the mechanically formed solutions may be performed by placing the sheet into an oven for a predetermined period of time. However formed, in preferred embodiments the reinforcing layer 14 is about 1 mm thick, with a range of about 0.5 to 2.0 mm. However, the layer 14 may be made from one or more other biocompatible materials, such as chitosan, natural autograft, allograft or xenograft tissue, synthetic degradable polymers such as PLA, PGA, PLGA or POE, or calcium phosphate.

In certain preferred embodiments the porous matrix 12 is made from a highly porous, collagen-ceramic composite material. The collagen-ceramic material may be initially created as a slurry which is then poured into a mold with the layer 14 and then freeze-dried to create the porous structure within the matrix 12. Other materials, however, may be suitable for the matrix 12, such as those indicated above.

In a specific embodiment the matrix 12 is made from collagen (10 to 30% by dry wt.) and calcium phosphate (55 to 89% by wt.). Preferably, the calcium phosphate is provided in granules having a diameter of between 0.1 to 5 mm, or, more preferably, 0.5 to 1.6 mm. The calcium phosphate may be provided in one or more chemical forms. In one embodiment, biphasic calcium phosphate is used. Optionally, the calcium phosphate may contain hydroxyapatite. In one embodiment, a biphasic calcium phosphate (BCP) bioceramic is used. BCP includes an intimate mixture of hydroxyapatite (HA), $Ca_{10}(PO_4)_6(OH)_2$, and beta-tricalcium phosphate (beta-TCP), $Ca_3(PO_4)_2$, in varying HA/beta-TCP ratios. In a specific embodiment the preferred HA/beta-TCP ratios are in the range of about 15/85 to about 25/75.

The composition of the collagen may also vary in different embodiments. In one embodiment, the collagen consists of a fibular collagen. Fibular collagen is precipitated collagen into highly organized relatively strong fibular strands during it's processing from digested collagen donor tissues such as skin and tendon.

In other embodiments the collagen includes about 20 to 40% by weight of soluble collagen and about 60 to 80% by weight of a more organized insoluble form of fibular collagen. The soluble collagen may increase the flowability and cohesiveness of the resultant slurry. The collagen, admixed with the calcium phosphate and a suitable fluid, provides a slurry that may be disposed within the layer 14, preferably using a shaped mold loaded with the layer 14 to provide the desired shape of the matrix 12. Suitable fluids for creating the slurry include for example reverse osmosis water. The volume of fluid used to create the slurry may be 75 to 99% the volume within the layer 14, with the balance being the collagen/ceramic material. The entire substitute 10 may then be freeze dried (i.e., lyophilized) to create the porous structure within the matrix 12. The preferred composition of matrix 12 maybe the same as other known matrices, such as the Mastergraft® Matrix, except possibly with slightly higher ratios of HA/TCP (such as 15/85 to 25/75).

The matrix 12 also allows for optimal loading of its porous structure with bioactive agents. Suitable bioactive agents include, without limitation, growth factors (including osteogenic and chondrogenic agents), anti-inflammatory agents, pain-reducing agents, antibiotics, cells, nucleic acid sequences, and any combinations thereof.

Suitable growth factors include but are not limited to bone morphogenic proteins, for example, BMP-2, rhBMP-2, BMP-4, rhBMP-4, BMP-6, rhBMP-6, BMP-7[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) Science, 242(4885):1528-1534. In one embodiment, the matrix 12 contains an effective amount of a BMP-2 protein, an rhBMP-2 protein, functional fragments thereof, or combinations thereof. The range of concentrations of BMP-2 may be about 1.0 to 4.0 mg/ml. GDF-5 concentrations may be 0.25 to 4.0 mg/ml. Although the matrix 12 may be loaded during manufacturing, it is ideally loaded just prior to implantation. If the matrix 12 is loaded during manufacturing, such bioactive agents may be added into the slurry prior to freeze-drying.

Suitable antibiotics include, without limitation, nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The various compounds encompassed by anti-inflammatories are well-known to those skilled in the art. For a detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974).

Mixtures of these non-steroidal anti-inflammatory compounds may also be employed, as well as the pharmologically acceptable salts and esters of these compounds.

In addition, so-called "natural" anti-inflammatory compounds may be useful. Such compounds may be obtained as an extract by suitable physical and/or chemical isolation from natural sources (e.g., plants, fungi, by-products of microorganisms). Suitable non-limiting examples of such compounds include candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora mukul*), kola extract, chamomile, sea whip extract, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Generally, anti-inflammatory non-steroidal drugs are included in the definition of pain-reducing agents because they provide pain relief. In addition, suitable pain-reducing agents include other types of compounds, such as, for example, opioids (such as, for example, morphine and naloxone), local anaesthetics (such as, for example, lidocaine), glutamate receptor antagonists, α-adrenoreceptor agonists, adenosine, canabinoids, cholinergic and GABA receptors agonists, and different neuropeptides. A detailed discussion of different analgesics is provided in Sawynok et al., (2003) Pharmacological Reviews, 55:1-20.

Suitable cells include, without limitations, stem cells, e.g., embryonic or adult stem cells, which can conveniently be derived from the blood or bone marrow of the patient or from an allogeneic source, which preferably is immunologically compatible with the patient. Other suitable cells may include chondrogenic or osteogenic precursor cells. A person of the ordinary skill in the art will appreciate that the cells may be genetically modified (e.g., overexpressing certain proteins, or having expression of certain proteins inhibited). Methods of creating such genetically modified cells are within knowledge and expertise of the person of ordinary skill in the art.

Suitable nucleic acid sequences include, without limitation, cDNA sequences encoding the at least one bioactive factor of a proteinaceous nature. These cDNAs may be included within respective vectors (e.g., AAV). In another embodiment, the nucleic acid sequences may be siRNAs or shRNAs or nucleic acid sequences encoding for such siRNAs or shRNAs. These siRNAs and shRNAs may be used in embodiments wherein it is desirable to inhibit expression of certain genes, such as, for example inflammatory protein genes such as TNF, IL-1, IL-6, and BMP inhibitor proteins such Noggin and Chordin, and intracellular BMP inhibitors SMADS. A person of ordinary skill in the art will appreciate that the nucleotide sequences for such genes are available in publicly-accessible databases, including, without limitation, Genbank. Further, the criteria for the siRNA selection have also been described in the art. Accordingly, a person of ordinary skill in the art will have sufficient knowledge and expertise in preparing such siRNAs or shRNAs.

Methods of incorporating the at least one bioactive factor are also known in the art. In one embodiment, the matrix 12 may be soaked in a solution of the at least one bioactive factor before implantation. In some embodiments, depending on the properties of the at least one bioactive factor, the matrix 12 may be soaked in the solution for 1 to 60 minutes before implantation. The at least one bioactive factor may also be dripped, brushed, or sprayed onto the matrix 12. In one specific embodiment the substitute 10 would be hydrated with a bioactive factor that is 50% of the matrix 12 volume, as larger volumes of solution may be easily lost during implantation of the substitute 10.

If the at least one bioactive factor includes cells, the cells may be re-suspended in a volume of media (e.g., Dulbecco's Modified Eagle's Medium) and cultured with the matrix 12. In a preferred embodiment the cells are applied during, or just before, implantation. In another embodiment the cells are cultured on the matrix. Due to the properties of the surface of the matrix 12 and the porosity of the matrix 12, the cells will populate the external surfaces of the matrix 12 and its internal voids (pores). Optimal loading conditions (e.g., medium composition, shaking, if necessary) may be easily determined by the person of ordinary skill in the art. Further, if only cells are being used instead of a bioactive factor the matrix 12 may be wetted with an aspirate from the patient's bone marrow, thus allowing the bone marrow cells to populate the voids and pores within the substitute 10. In this embodiment once matrix 12 is hydrated additional solutions are not applied. If both cells and bioactive factors are desired then the total solution volumes of each should not exceed the porous volume of matrix 12.

As previously indicated, a slurry that forms the matrix 12 may be poured or otherwise disposed within the reinforcing layer 14 and subsequently freeze-dried to form the bone graft substitute 10. Alternatively, the matrix 12 may be formed separately and then subsequently bonded to the layer 14. A preferred bonding process of the matrix 12 to the layer 14 provides for chemically bonding with formaldehyde vapor or thermal bonding. In this process the collagen of the matrix 12 will bond to the collagen (or chitosan) in the layer 14. The matrix 12 may be loaded with one or more bioactive agents, such as rhBMP-2, either before or after such a bonding step.

Figure 2:
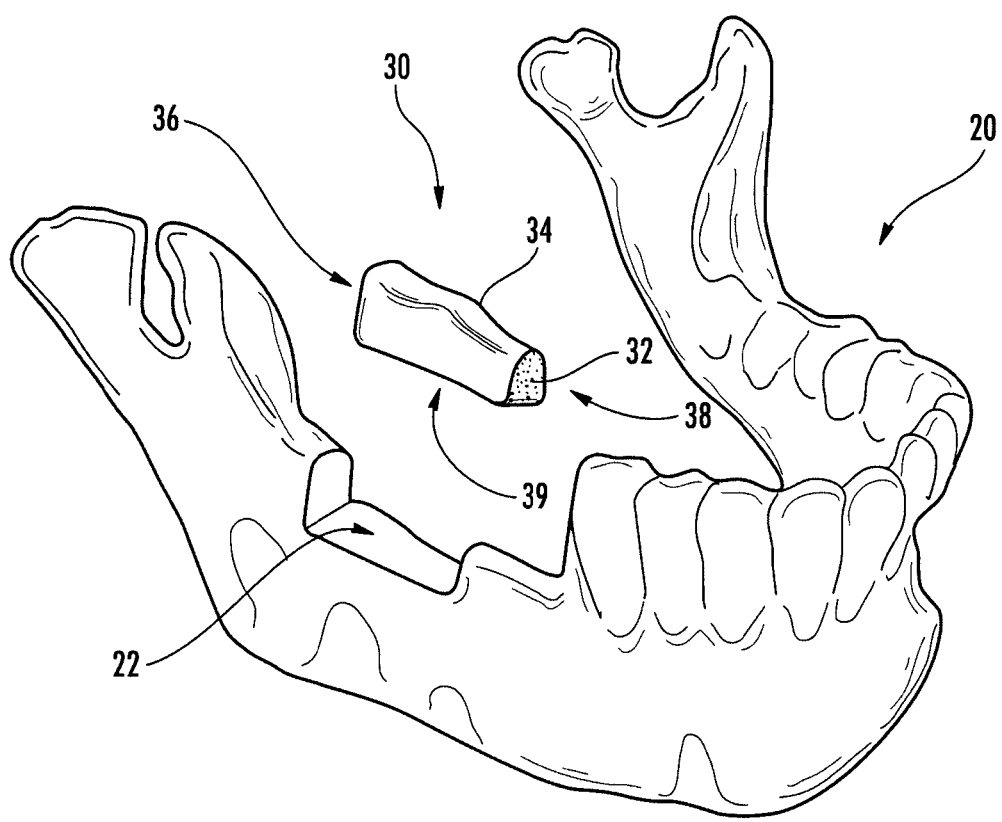
FIG. 2 is a perspective view of a second embodiment bone graft substitute being positioned near a target region for implantation.
Figure 3A:
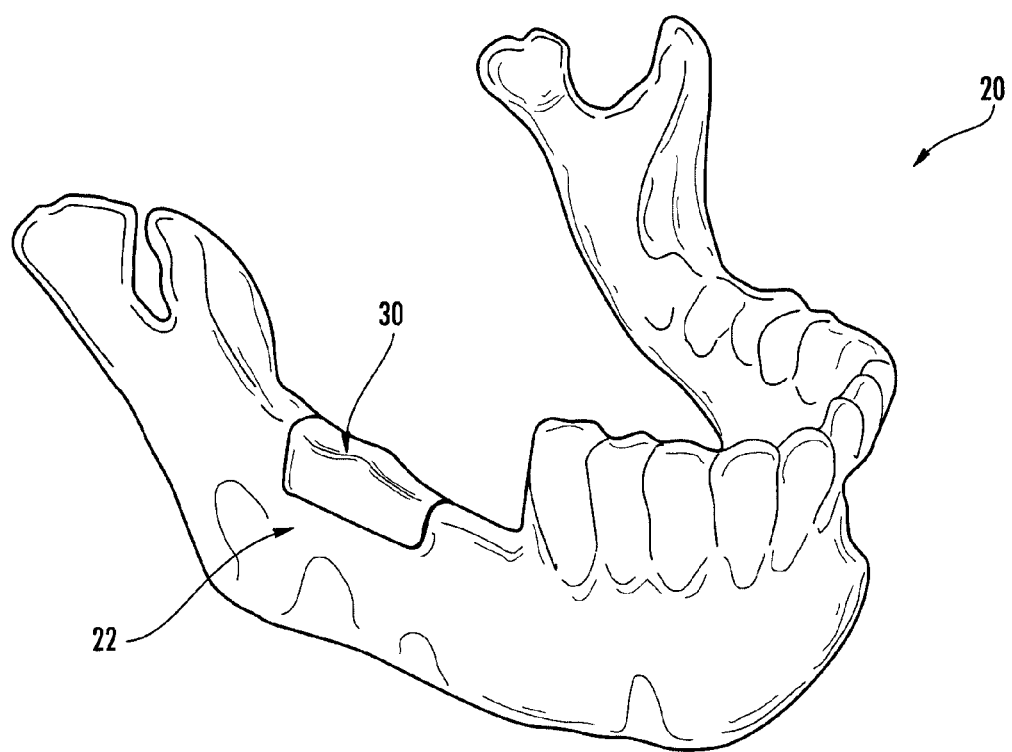
FIG. 3A is a perspective view showing the bone graft substitute of FIG. 2 disposed within the target region.
Figure 3B:
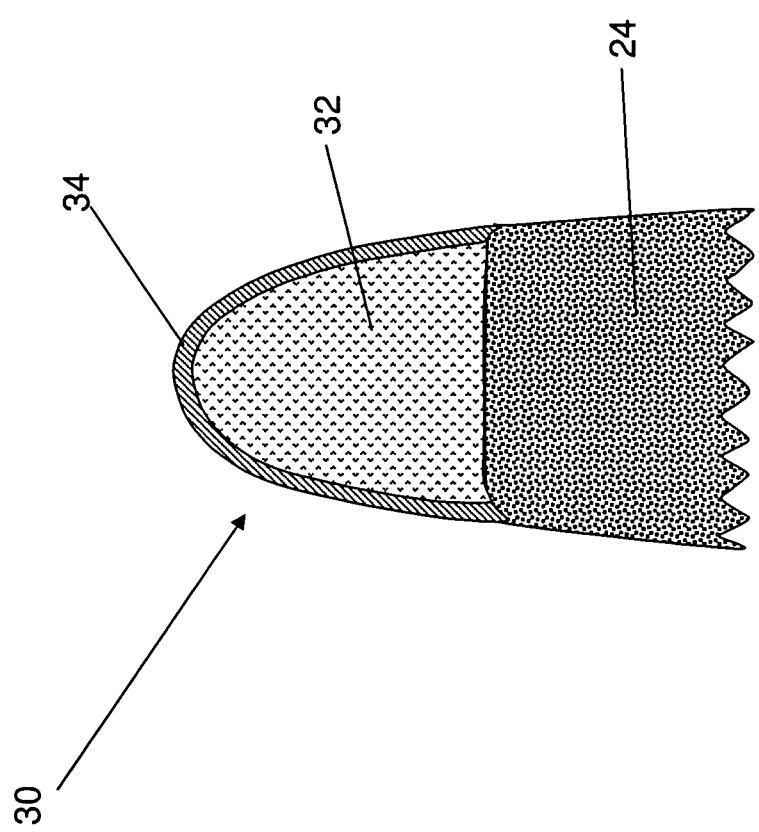
FIG. 3B is a cross-sectional view showing the bone graft substitute of FIG. 2 disposed within the target region.

The reinforcing layer 14 provides mechanical support to the matrix 12 so that the substitute 10 maintains its shape as new bone is formed of sufficient volume within the matrix 12. For example, with reference to FIG. 2, a bone defect 22 is present within the jawbone 20 of a patient. Bone defect 22 is thus a target site at which the growth of bone is desired to repair the defect 22. An embodiment bone graft substitute 30 may be designed to have a shape that is conformal with the target site 22, or close to the shape of target site 22. For example, multiple volume sizes of implants (1 cc, 2 cc, 5 cc, 10 cc, 15 cc, 20 cc) may be provided for use to best match the size of the bone defect 22. The implant size selected may be one that best matches the height of the defect 22, cutting the base if needed to make the implant 30 fit better. The width of the implant 30 may then be compressed to fit the width of the base of the bone defect 22. The substitute 30 has a reinforcing outer layer 34 that partially surrounds a porous matrix 32. In particular, the layer 34 surrounds all external surfaces of the matrix 32 but for those external surfaces 32 that will be immediately adjacent to, or in contact with, bone at the target site 22. For example, ends 36, 38 and bottom 39 of matrix 32 are preferably open (i.e., not covered by layer 34 and hence exposed) so that host bleeding bone surfaces can grow rapidly into matrix 32. Hence, as shown in FIG. 3A, when the substitute 30 is disposed within the target site 22, the substitute 30 appears to be substantially completely covered by the layer 34 when disposed within the target site 22, and, as shown in FIG. 3B, exposed regions of the matrix 32 are disposed immediately adjacent to, or in contact with, bone 24.

Figure 4:
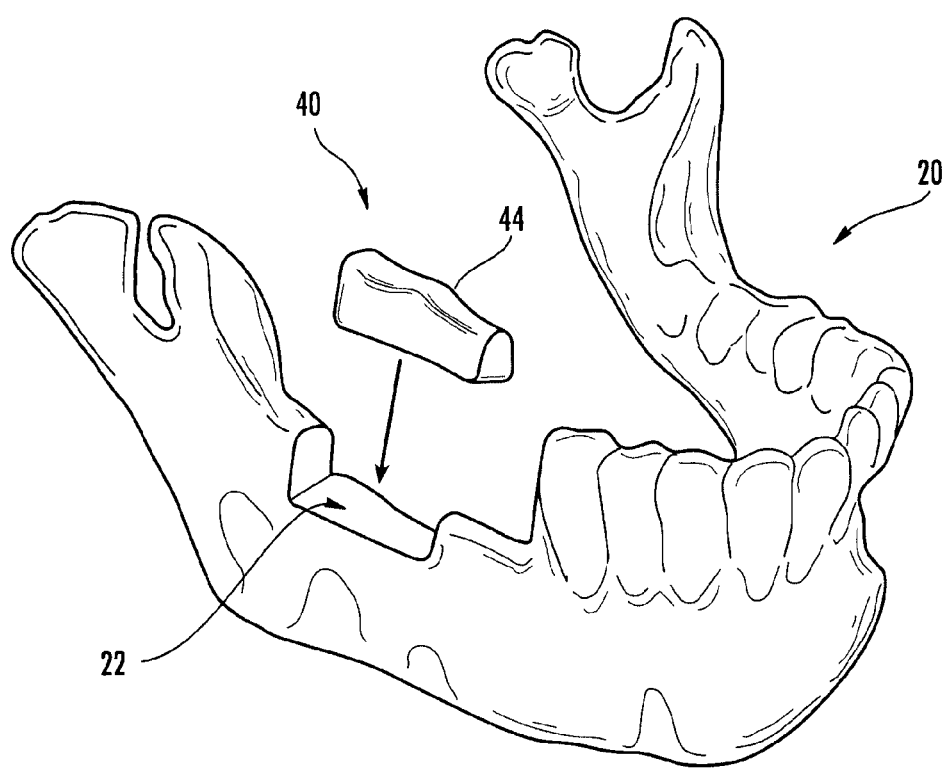
FIG. 4 is a perspective view of a third embodiment bone graft substitute being positioned near a target region for implantation.

An alternative embodiment bone graft substitute 40 is shown in FIG. 4. By way of example, the same jawbone 20 with defect 22 is shown. Substitute 40 is shaped to conform to defect 22, and has a porous matrix (not shown) that is completely surrounded by reinforcing outer layer 44. As indicated in FIG. 4, substitute 40 may be disposed within defect 22 to fill defect 22. Because the outer layer 44 completely encloses the relatively pliant inner matrix, substitute 40 may provide greater structural strength and rigidity than embodiment substitute 30.

Figure 5:
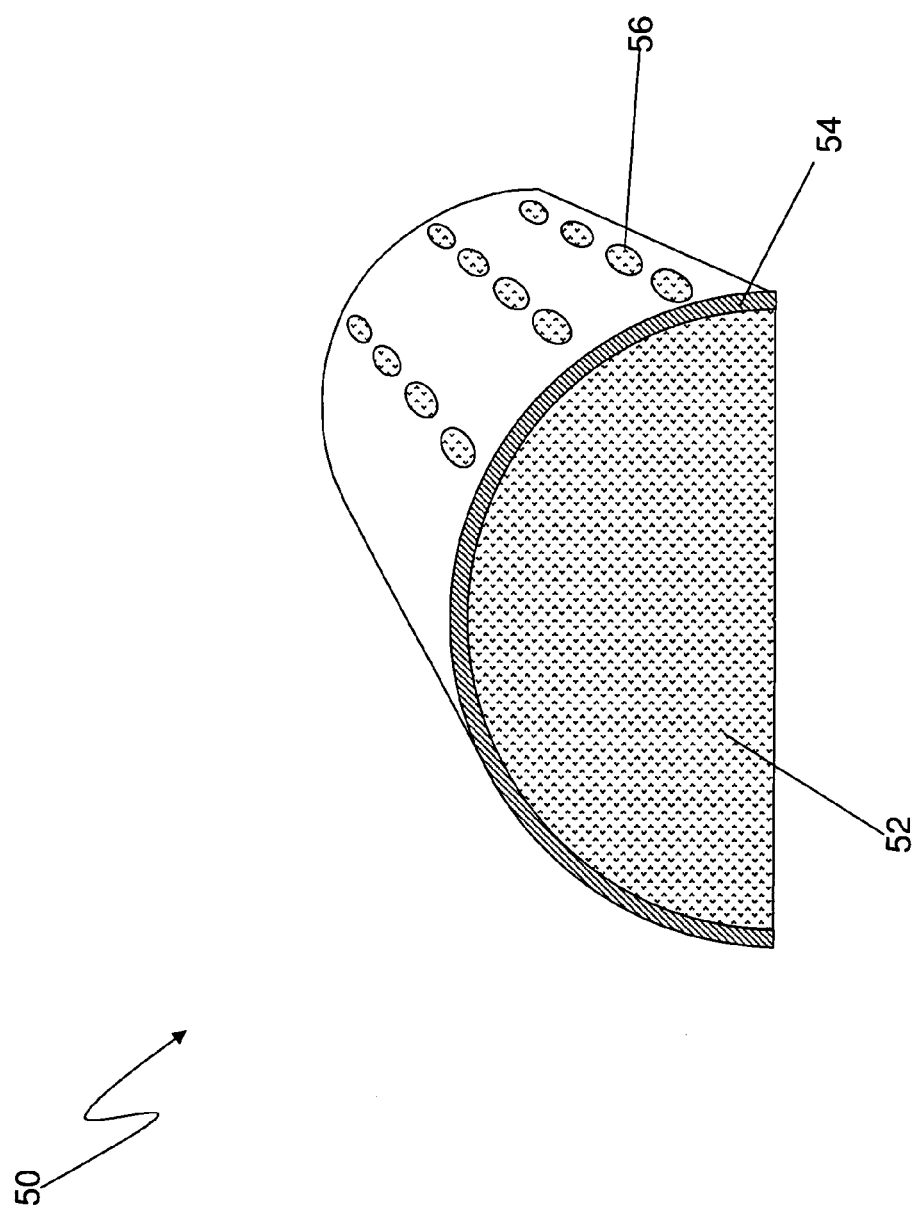
FIG. 5 is perspective view of a fourth embodiment bone graft substitute.
Figure 6:
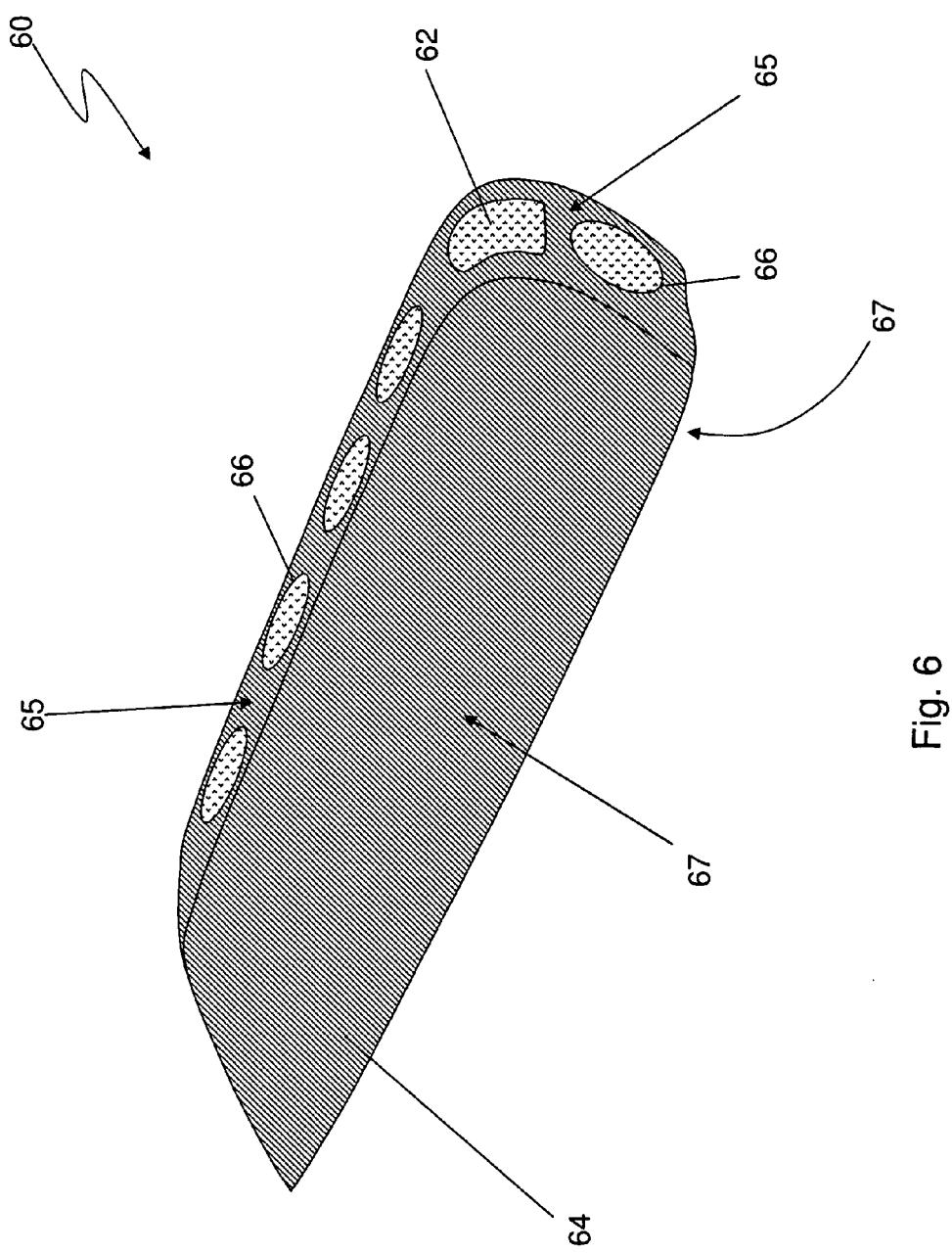
FIG. 6 is perspective view of a fifth embodiment bone graft substitute.

It is not necessary that the outer layer be wholly continuous. For example, as shown in FIG. 5, an embodiment implant 50 may have a reinforcing outer layer 54 that at least partially surrounds a porous matrix 52, and which has one or more openings 56 that further expose the inner matrix 52. In a preferred embodiment the openings 56 may be formed when the outer layer 54 is formed. In an alternative embodiment, the openings 56 may be formed subsequently, as by drilling, etching or any other suitable method. The one or more openings 56 in the layer 54 may provide for the ingress of fluids, cells, blood vessels and the like into the inner matrix 52. Certain embodiment bone graft substitutes may have outer layers that completely surround and enclose the inner matrix, but which further comprise openings to partially expose the inner matrix. By way of example, the openings may be larger or more closely spaced for those regions of the outer layer that will be immediately adjacent to or in contact with bone at the target site, whereas those other portions of the layer may have openings that are smaller or more distantly spaced from each other. For example, as shown in FIG. 6, an embodiment bone graft substitute 60 may have an outer layer 64 with surfaces 65 having openings 66, in which the surfaces 65 will be immediately adjacent to, or in contact with, bone at the target site. The openings 66 expose inner matrix 62. Surfaces 67 that will not be immediately adjacent to or in contact with bone at the target site are solid, without any openings 66. In alternative embodiments, the surfaces 67 may also have openings 66, but these openings may be smaller or more widely separated from each other. In yet other embodiments, the size and space of the openings 66 may be substantially equal across the entire outer layer 64.

To provide even greater structural strength, embodiment implants may further include reinforcement ribs. The reinforcement ribs are made from a biocompatible material, and preferably from a biodegradable material. In certain preferred embodiments, the reinforcement ribs are made from a calcium phosphate ceramic, such as tri-calcium phosphate (TCP), or a ratio of HA/TCP of 15/85 to 25/75. In other embodiments, the reinforcement ribs are made from dense collagen. This dense collagen preferably has a relatively low porosity, such as less than 65% porous. In specific embodiments, the collagen ribs have a porosity of 0 to 65%. The collagen ribs may be made integrally with the outer layer, for example by pouring a collagen slurry into flat sheet trays with ribs in them in which thicker ribs of collagen are formed. The sheet may then be freeze-dried or air-dried and formed into the desired shape prior to chemically or thermally cross-linking into the final shape. However, other materials, including materials that are not biodegradable, may be used for the reinforcement ribs. Exemplary materials include, but are not limited to, HA ceramics, chitosan, and nondegradable polymers such as polyethylene, delrin, and teflon.

If not integrally formed with the outer layer, the reinforcement ribs may be added to the outer layer during or after the formation of the outer layer. The porous matrix may then be added to the resultant structure to form an embodiment implant. For example, a dense outer layer of collagen may first be formed, as by molding or machining, to provide the general shape of at least a portion of the external surfaces of the bone graft substitute. Reinforcement ribs of, for example, TCP may then be added to the outer layer. By way of example, reinforcement ribs of TCP may be laid where desired on the layer just prior to applying the collagen-ceramic slurry, which will then hold the ribs in place. The collagen-ceramic slurry may be poured into a mold containing this combined outer layer and reinforcement ribs. Regardless of whether or not reinforcement ribs are used, in certain embodiments, depending upon the shape of the outer layer, a mold may not be needed when pouring the slurry into the outer layer. For example, if the outer layer forms a hollow region, the slurry may be poured or injected into this hollow region without requiring a mold. Subsequently, the combination is freeze-dried to provide the porous inner matrix and final shape of the bone graft substitute.

Figure 7:
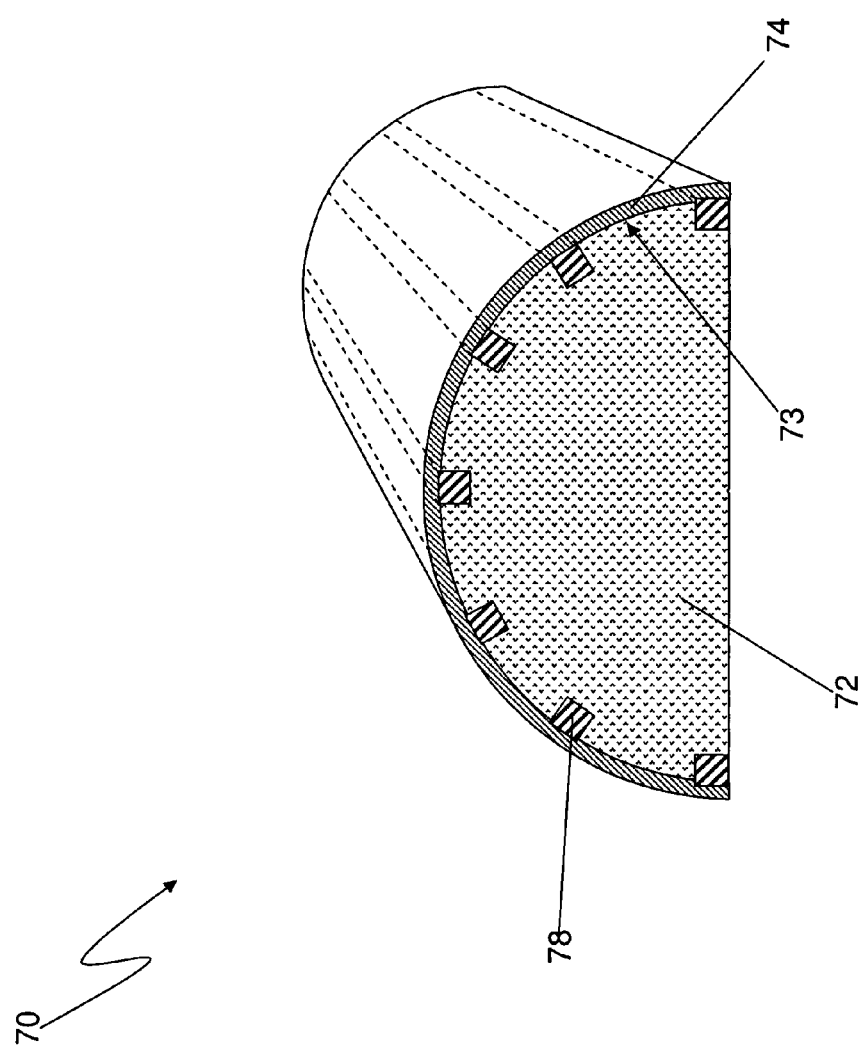
FIG. 7 is perspective view of a sixth embodiment bone graft substitute.
Figure 8:
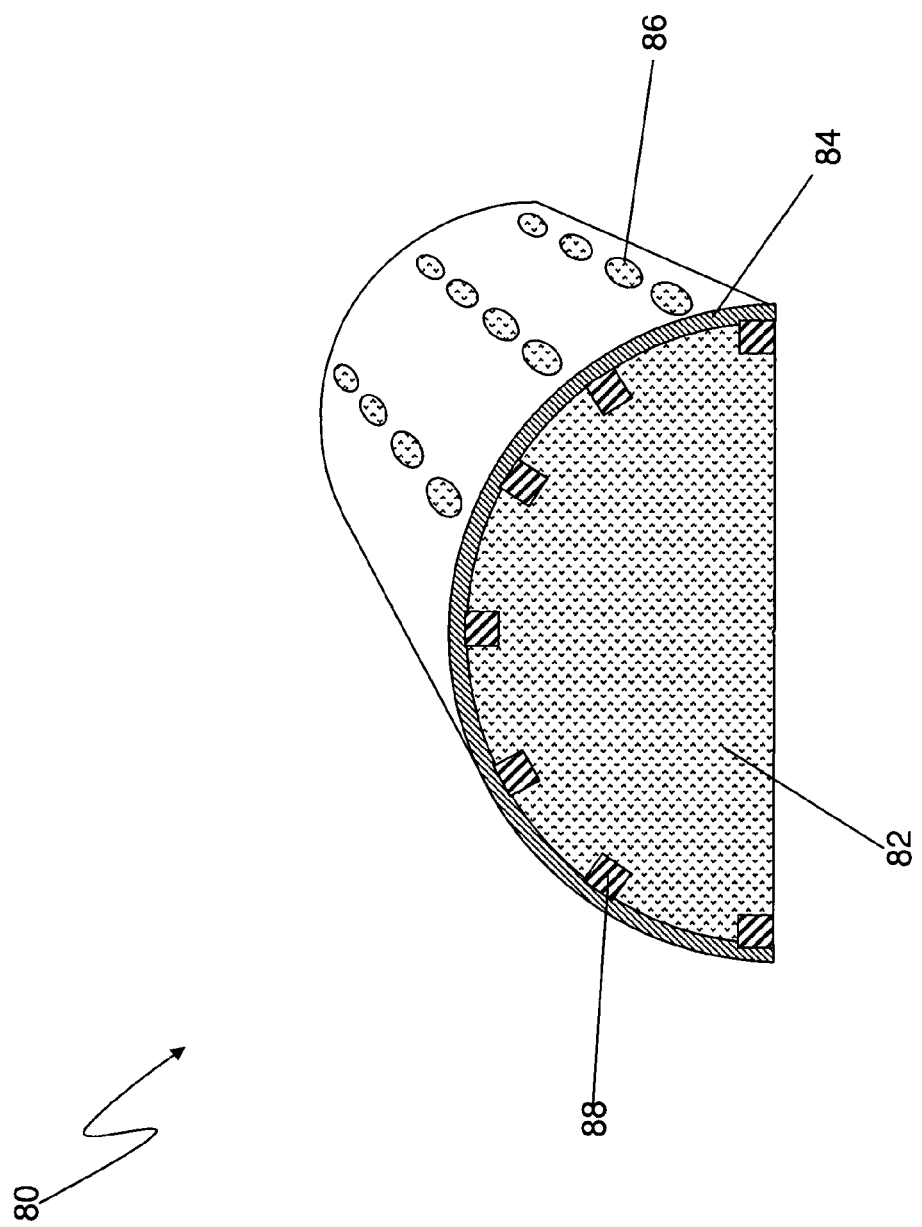
FIG. 8 is perspective view of a seventh embodiment bone graft substitute.

An embodiment bone graft substitute 70 having ribs 78 is shown in FIG. 7. The substitute 70 may include a reinforcing outer layer 74, such as of highly cross-linked collagen, that at least partially surrounds a porous inner matrix 72, such as of a collagen-ceramic material. Disposed along the inside surface 73 of outer layer 74 are one or more reinforcement ribs 78, such as of TCP. The ribs 78 are thus fully enclosed by the outer layer 74 and the inner matrix 72. The ribs 78 may extend along the entire length of the implant 70, or may extend along only a portion of the length of implant 70. The ribs 78 may all run along the generally same axis of orientation, may each run perpendicular to this axis of orientation, or each have its own axis along which it runs. The number and placement of the ribs 78 is a design choice well within the means of one having ordinary skill in the art. Another bone graft substitute 80 is shown in FIG. 8 that further includes openings 86 in reinforcing outer layer 84 to further expose inner matrix 82, as well as having reinforcement ribs 88 to provide additional structural strength to the implant 80.

Figure 9:
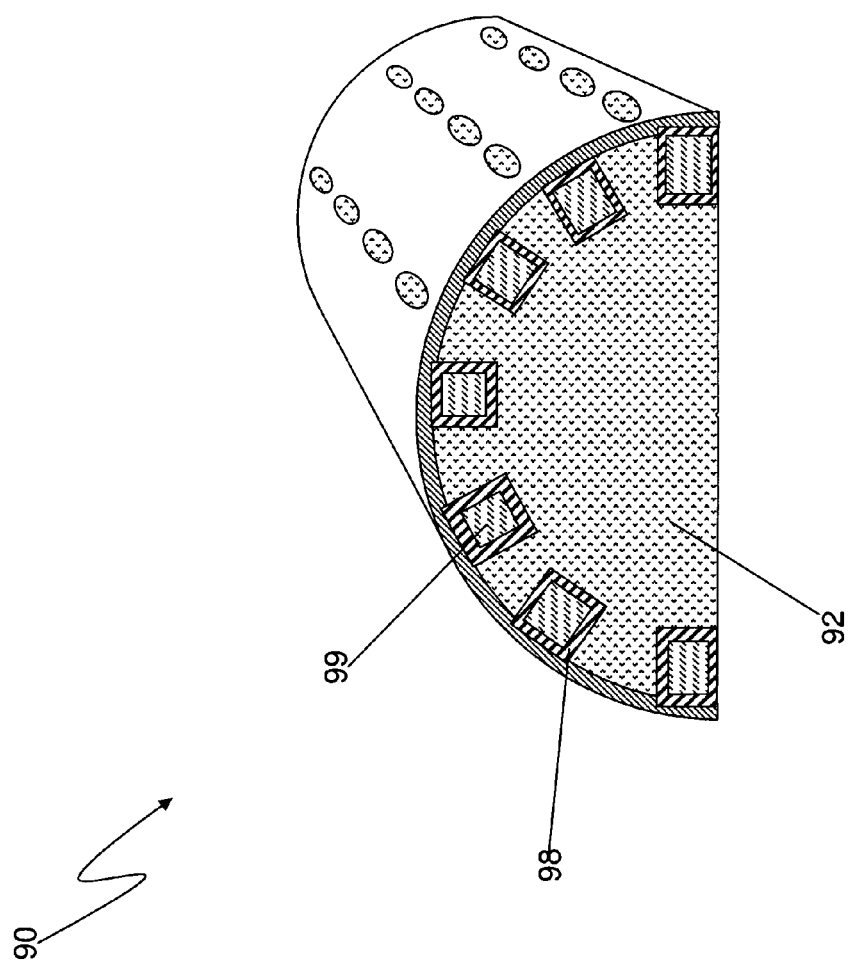
FIG. 9 is perspective view of a eighth embodiment bone graft substitute.
Figure 10:
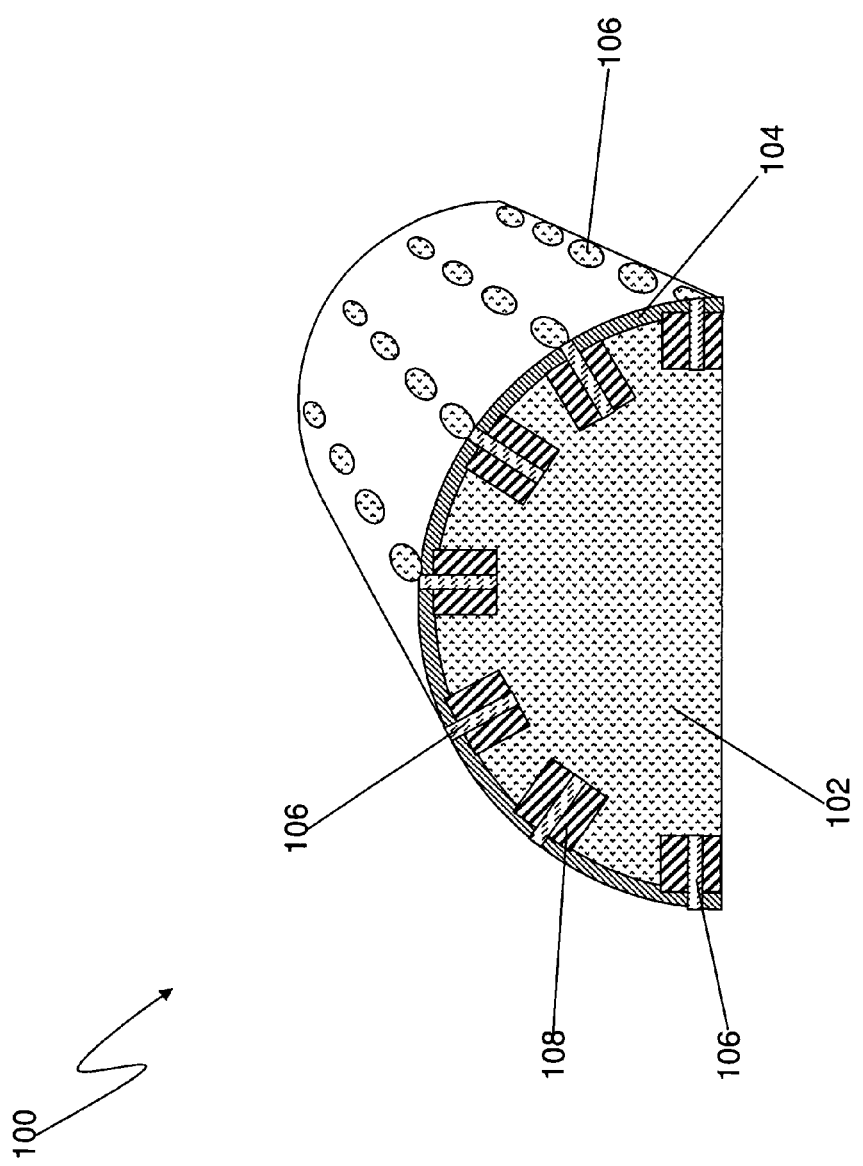
FIG. 10 is perspective view of a ninth embodiment bone graft substitute.
Figure 11:
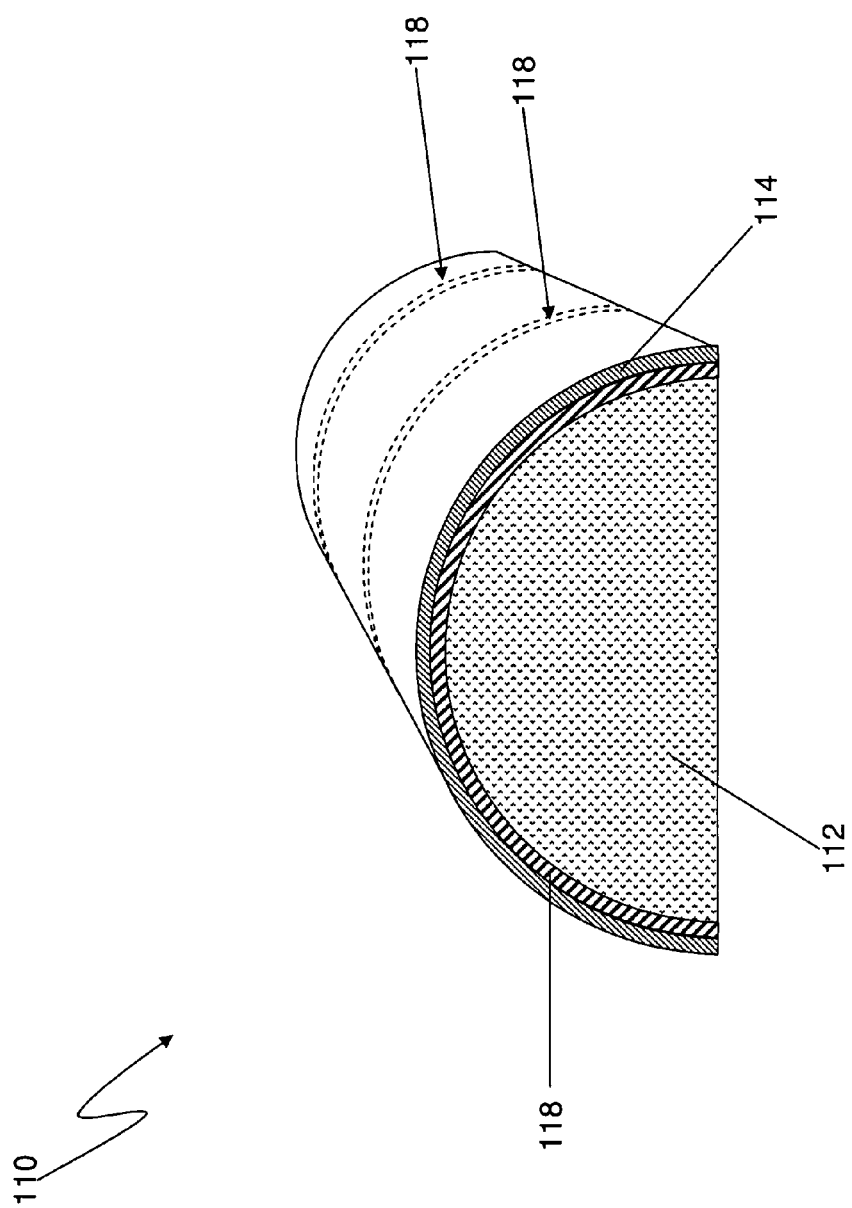
FIG. 11 is perspective view of a tenth embodiment bone graft substitute.

To provide for additional bone ingrowth into the implant, certain embodiment bone graft substitutes may have reinforcement ribs that also have holes, openings or hollow regions. These sections within the ribs may be provided without significantly affecting the structural strength of the implant. FIG. 9 shows an embodiment bone graft substitute 90 having ribs 98 with hollow regions 99. The hollow regions 99 may run the entire length of the ribs 98, or may be in only a portion of the ribs 98. For example, a rib 98 may have a plurality of spaced hollow regions 99. The side walls of these hollow regions may also have holes to further expose the hollow regions. In some embodiments, the hollow regions 99 may be filled with the matrix material 92. Hence, a reinforcement rib may present as a porous structure through which access to the inner matrix may be obtained. Yet another embodiment bone graft substitute 100 is shown in FIG. 10 that has openings 106 in reinforcing outer layer 104 to further expose inner matrix 102. The substitute 100 has solid reinforcement ribs 108 to provide additional structural strength to the implant 100, and at least some of the openings 106 pass through the ribs 108 to expose the matrix 92. Of course, the ribs are not limited to simply running down along the longitudinal length of the bone graft substitute, as indicated earlier. To the contrary, the ribs may run along any axis or path. For example, as shown in FIG. 11, an embodiment 110 may include ribs 118 that are aligned perpendicular to the longitudinal axis of implant 110, and run along an arcuate path. The ribs 118 rest disposed between the porous inner matrix 112 and the reinforcing outer layer 114.

Figure 12:
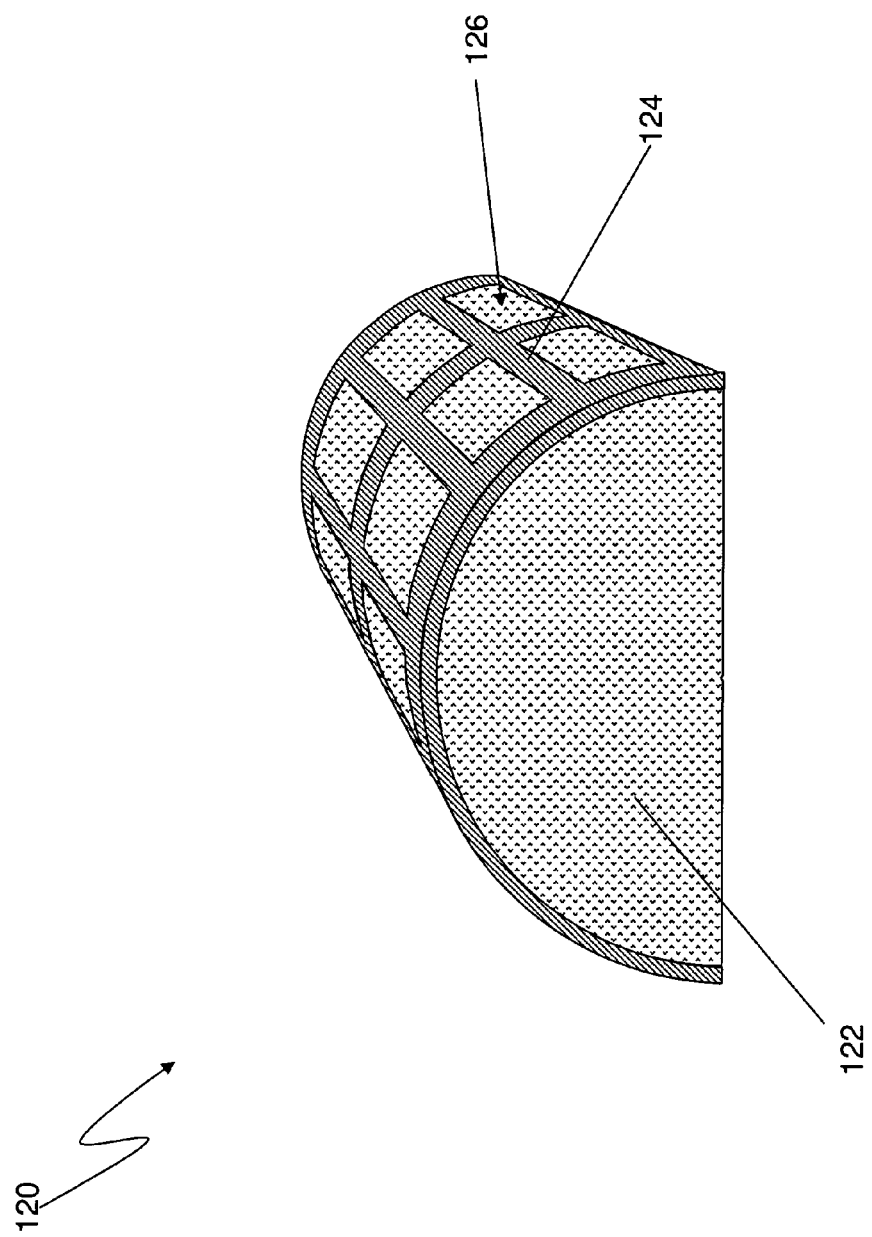
FIG. 12 is a perspective view of an eleventh embodiment bone graft substitute.

In certain embodiments, either with or without reinforcement ribs, the surface of the openings within the reinforcing outer layer may be a substantial fraction of, or even exceed, the surface area of the reinforcing outer layer itself. For example, as shown in FIG. 12, an embodiment substitute 120 has an outer layer 124 made of highly cross-linked collagen, and a porous inner matrix 122. The outer layer 124 has several large openings 126 that expose the matrix 122. The external surface area of the openings 126 may equal or exceed the external surface area of the outer layer 124. Hence, the outer layer 124 effectively forms a scaffolding around the matrix 122.

It will be appreciated that the various embodiment bone graft substitutes are not merely limited to placement within jawbones. Embodiment implants may be suitable in any location where mechanical strength, rigidity or both are required, including cranial skull defects, segmental defects, and diaphyseal and metephyseal bone defects. Moreover, the implants may be provided any suitable shape, both regular and irregular. Although it is preferred that the shape of the bone graft substitute substantially conform to the target site so as to provide a snug fit within the target site and to maximally fill all regions in which bone growth is desired, it will be appreciated that such conformal fits are not necessarily required of the embodiment bone graft substitutes. The embodiment implants may have any suitable shape such as cylinders.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A bone graft substitute comprising: a porous matrix; a reinforcing outer layer covering at least a portion of the porous matrix and having at least one opening providing access to the porous matrix, the reinforcing outer layer having an inside surface; and a plurality of reinforcement ribs disposed along the inside surface of the reinforcing outer layer along the entire length of the bone graft substitute, each reinforcement rib of the plurality of reinforcement ribs being surrounded by and contacting the porous matrix on at least three sides and the inside surface of the reinforcing outer layer, and each reinforcement rib of the plurality of reinforcement ribs comprising four side walls, the four side walls defining a hollow region that runs the entire length of the reinforcement rib, the four side walls comprising holes to further expose the hollow region, wherein the plurality of reinforcement ribs comprise a biodegradable material and are integrally formed with the outer layer, and the porous matrix comprises a bioactive agent comprising BMP-2 at a concentration from about 1.0 to 4.0 mg/ml, and the at least one opening is disposed between the plurality of reinforcement ribs.

2. The bone graft substitute of claim 1 wherein the porous matrix is a collagen-ceramic composite.

3. The bone graft substitute of claim 2 wherein the collagen-ceramic composite further comprises calcium phosphate.

4. The bone graft substitute of claim 1 wherein the reinforcing outer layer is formed from highly cross-linked collagen.

5. The bone graft substitute of claim 1 wherein the reinforcement ribs comprise calcium phosphate or dense collagen.

6. The bone graft substitute of claim 1 wherein the bioactive agent further comprises rhBMP-2, BMP-4, rhBMP-4, BMP-6, rhBMP-6, BMP-7, rhBMP-7, GDF-5, rhGDF-5, functional fragments thereof, and combinations thereof.

7. The bone graft substitute of claim 1, wherein the plurality of reinforcement ribs comprise TCP (tri-calcium phosphate).

8. The bone graft substitute of claim 1, wherein the porous matrix comprises macropores that are 25 to 1000 microns in size and the porous matrix comprises micropores that are 0.1 to 5 microns in size.

9. A bone graft substitute comprising: a porous matrix, the porous matrix comprising collagen from about 10 wt. % to about 30 wt. % and calcium phosphate from about 55 wt. % to 89 wt. %, the calcium phosphate having a diameter from about 0.1 mm to about 5 mm; a reinforcing outer layer covering at least a portion of the porous matrix and having a plurality of openings providing access to the porous matrix, the openings occupying more than 50% of the reinforcing outer layer, the reinforcing outer layer having an inside surface; and reinforcement ribs disposed along the inside surface of the reinforcing outer layer, the reinforcement ribs being surrounded by and contacting the porous matrix on at least three sides and the inside surface of the reinforcing outer layer, and each of the reinforcement ribs comprising four side walls, the four side walls defining the boundary of a hollow region, the reinforcement ribs contacting at least one opening of the reinforcing outer layer that allows access to the porous matrix, the reinforcement ribs running perpendicular to a longitudinal axis of the bone graft substitute, the reinforcement ribs comprising holes to further expose the hollow region, wherein the reinforcement ribs comprise a biodegradable material and are integrally formed with the outer layer, and the porous matrix comprises a bioactive agent comprising BMP-2 at a concentration from about 1.0 to 4.0 mg/ml.

10. The bone graft substitute of claim 9 wherein the reinforcing outer layer is formed from highly cross-linked collagen.

11. The bone graft substitute of claim 9 wherein the reinforcement ribs comprise calcium phosphate or dense collagen.

12. The bone graft substitute of claim 9 wherein the bioactive agent further comprises rhBMP-2, BMP-4, rhBMP-4, BMP-6, rhBMP-6, BMP-7, rhBMP-7, GDF-5, rhGDF-5, functional fragments thereof, and combinations thereof.

* * * * *